(12) United States Patent
Shevchenko et al.

(10) Patent No.: US 7,842,165 B2
(45) Date of Patent: Nov. 30, 2010

(54) ENHANCED METHOD FOR MONITORING THE DEPOSITION OF ORGANIC MATERIALS IN A PAPERMAKING PROCESS

(75) Inventors: Sergey M. Shevchenko, Aurora, IL (US); Michael J. Murcia, Aurora, IL (US); Rodney H. Banks, Aurora, IL (US)

(73) Assignee: Nalco Company, Naperville, IL (US)

( * ) Notice: Subject to any disclaimer, the term of this patent is extended or adjusted under 35 U.S.C. 154(b) by 587 days.

(21) Appl. No.: 11/846,920

(22) Filed: Aug. 29, 2007

(65) Prior Publication Data

US 2009/0056897 A1    Mar. 5, 2009

(51) Int. Cl.
*D21H 23/08*    (2006.01)
(52) U.S. Cl. ...................... 162/198; 162/263
(58) Field of Classification Search .......... 162/198, 162/199, 263, 272, 274, 4, 5; 73/61.45, 61.49, 73/61.61, 61.62, 61.75, 61.79, 64.53
See application file for complete search history.

(56) References Cited

U.S. PATENT DOCUMENTS

| | | | |
|---|---|---|---|
| 3,266,291 A * | 8/1966 | King, Jr. ............... | 73/24.06 |
| 4,399,686 A * | 8/1983 | Kindlund et al. ......... | 73/24.06 |
| 5,589,396 A * | 12/1996 | Frye et al. ............... | 436/73 |
| 6,357,278 B1 * | 3/2002 | Sivavec et al. ........... | 73/24.01 |
| 6,375,829 B1 | 4/2002 | Shevchenko et al. | |
| 6,942,782 B2 | 9/2005 | Shevchenko et al. | |
| 7,449,086 B2 * | 11/2008 | Gray et al. ............... | 162/181.6 |
| 2006/0281191 A1 * | 12/2006 | Duggirala et al. ......... | 436/178 |

OTHER PUBLICATIONS

Tsuji, H. et al. "Method for Measuring Microstickies Using Quartz Crystal MicroBalance with Dissipation Monitoring." Kami Parupu Kenkyu Happyokai Koen Yoshishu 73, 126-129 (2006).

* cited by examiner

*Primary Examiner*—Eric Hug
(74) *Attorney, Agent, or Firm*—Joshua D. Bishop; Michael B. Martin (57) ABSTRACT

A method for monitoring the deposition of one or more organic materials dispersed in an aqueous medium in a papermaking process comprising: measuring the rate of deposition of the organic materials from the aqueous medium on-to a quartz crystal microbalance having a top side contacting with the aqueous medium coated with a layer containing a non-swelling epoxy resin or a silicone containing polymer, and a second, bottom side isolated from the aqueous medium is disclosed. Additionally, a method for measuring the effectiveness of an inhibitor that decreases the deposition of the organic materials in a papermaking process is also disclosed.

15 Claims, 6 Drawing Sheets

FIG. 1

Epoxy Crystal In Artificial Stickies Furnish with Surfactant (DVP60002) Treatment

FIG. 2

Artificial Stickies in Thin Stock With Surfactant Treatment

FIG. 3

Silicone Coated Crystal in Thin Stock with Artificial Stickies

FIG. 4

Surfactant Accumulation on Silicone Coated Crystal

FIG. 5

Stickies Deposition From Re-pulped Artificial Stickies Furnish

FIG. 6

Epoxy Coated and Uncoated Crystal in DI Water

FIG. 7

PVC and Epoxy Coated Crystals in Recycled Thin Stock

FIG. 8

Recycled Thin Stock - No Treatment

FIG. 9

Stickies Deposition From Whitewater

FIG. 10

Recycled Thin Stock Treated with DVP6O002

FIG. 11

Artificial Pitch Experiment

FIG. 12

LDPE-Coated Crystal in ThinStock

ENHANCED METHOD FOR MONITORING THE DEPOSITION OF ORGANIC MATERIALS IN A PAPERMAKING PROCESS

FIELD OF THE INVENTION

This invention is in the field of papermaking. Specifically, this invention is in the field of monitoring organic deposit formation in a papermaking process.

BACKGROUND OF THE INVENTION

Organic materials, such as pitch, stickies, and tackies, are major obstacles in paper manufacturing because these materials when liberated during a papermaking process can become both undesirable components of papermaking furnishes and troublesome to the mill equipment, e.g. preventing proper operation of mechanical parts when these materials deposit on the mechanical parts.

Deposition of organic materials on the surface of a quartz crystal microbalance sensor is known. However, due to the low affinity of a standard surface to hydrophobic organic materials, the rate of deposition is normally low.

An efficacious and enhanced method of monitoring the deposition of organic materials is thus desired. Furthermore, a method of monitoring the effectiveness of inhibitors that prevent/reduce deposition of organic materials in a papermaking process is also desired.

SUMMARY OF THE INVENTION

The present invention provides for a method for monitoring the deposition of one or more organic materials dispersed in an aqueous medium in a papermaking process comprising: measuring the rate of deposition of the organic materials from the aqueous medium on-to a quartz crystal microbalance having a top side contacting with the aqueous medium coated with a layer containing a cured non-swelling epoxy resin or a silicone containing polymer, and a second, bottom side isolated from the aqueous medium.

The present invention also provides a method for measuring the effectiveness of inhibitors that decrease the deposition of one or more organic materials in a papermaking process comprising: monitoring one or more organic materials dispersed in an aqueous medium in an actual or simulated papermaking process comprising measuring the rate of deposition of the organic materials from the aqueous medium onto a quartz crystal microbalance having a top side contacting the aqueous medium coated with a layer containing a non-swelling epoxy resin or a silicone containing polymer, and a second, bottom side isolated from the aqueous medium; adding an inhibitor that decreases the deposition of the organic materials from the aqueous medium; and re-measuring the rate of deposition of the organic materials from the aqueous medium onto the coated surface of the quartz crystal microbalance.

BRIEF DESCRIPTION OF THE DRAWINGS

The benefits and advantages of the present invention will become more readily apparent to those of ordinary skill in the relevant art after reviewing the following detailed description and accompanying drawings, wherein.

DETAILED DESCRIPTION OF THE INVENTION a. Definitions

"Papermaking process" means a method of making any kind of paper products (e.g. paper, tissue, board, etc.) from pulp comprising forming an aqueous cellulosic papermaking furnish, draining the furnish to form a sheet and drying the sheet. The steps of forming the papermaking furnish, draining and drying may be carried out in any conventional manner generally known to those skilled in the art. The papermaking process may also include a pulping stage, i.e. making pulp from woody raw material and bleaching stage, i.e. chemical treatment of the pulp for brightness improvement.

"QCM" means quartz crystal microbalance.

"SRM" means scale rate monitor. U.S. Pat. No. 6,375,829 and U.S. Pat. No. 6,942,782 describe Nalco's scale rate monitor, and are herein incorporated by reference. An SRM contains a QCM.

"RQCM" means research quartz crystal microbalance, which is commercially available from Maxtek, Inc., Cypress, Calif.

b. Preferred Embodiments

QCMs are known in the art of papermaking. SRMs and RQCMs are examples of types of instruments using QCMs. In one embodiment, the top side of the quartz crystal microbalance is made up of one or more conductive materials selected from the group consisting of: platinum; titanium; silver; gold; lead; cadmium; diamond-like thin film electrodes with or without implanted ions; silicides of titanium, niobium, and tantalum; lead-selenium alloys; mercury amalgams; and silicone.

Coating the top side of a quartz crystal microbalance with a layer containing a non-swelling epoxy resin or a silicone containing polymer facilitates adhesion of organic deposits to the surface of the quartz crystal microbalance.

A non-swelling epoxy resin applied to a quartz crystal microbalance has the characteristic of not substantially swelling in an aqueous environment, e.g. aqueous medium in a papermaking process. One of ordinary skill in the art can determine whether a resin is non-swelling without undue experimentation.

In one embodiment, the resin is selected from the group consisting of: a cresol-novolac epoxy resin; a phenol novolac epoxy resin; a bisphenol F (4,4'-, 2,4'- or 2,2'-dihydroxy-diphenylmethanes or a mixture thereof) epoxy resin; a polynuclear phenol-glycidyl ether-derived resin; a tetraglycidyl-methylenedianiline-derived resin; a triglycidyl-p-aminophenol derived resin; a triazine-derived resin; and a hydantoin epoxy resin.

In another embodiment, the resin is derived from epichlorohydrin and 4,4'-dihydroxy-2,2-diphenylpropane (bisphenol A; may also contain 2,4'- or/and 2,2'-isomers).

In another embodiment, the resin contains an aromatic backbone, aliphatic backbone, cycloaliphatic backbone, or a heterocyclic backbone.

A silicone containing polymer can also be applied to the surface of a quartz crystal microbalance.

In one embodiment, the silicone containing polymer is selected from the group consisting of: silicone rubber, and room temperature vulcanizing silicone rubber.

A coupling agent may be utilized to facilitate the adhesion of the resin to the QCM surface.

In one embodiment, the coupling agent is 3-glycidoxypropyltrimethox-silane, which is available from Dow Corning® Corporation, as DOW CORNING Z-6040® SILANE. DOW CORNING Z-6040® SILANE is a heterobifunctional coupling agent.

In a further embodiment, DOW CORNING Z-6040® SILANE is prepared as a 0.1-0.5% solution in acidified water and applied to the active face of the crystal, and then after applying the silane, the crystal is dried at 104° C.-121° C., resulting in an epoxide functionalized surface that is covalently linked to the quartz crystal. The surface is then coated with a thin layer of epoxy.

The epoxy resin and silicone containing polymer may be applied to the QCM surface by various methods that would apparent to one of ordinary skill in the art.

In one embodiment, the epoxy resin or silicone containing polymer are applied to the QCM surface by a drop coating method or a spin coating method.

After the epoxy resin or silicone containing polymer is applied to the QCM surface, the epoxy resin and silicone containing polymer are hardened/cured.

The epoxy resin is hardened/cured by a curing agent. The type of curing agent utilized would be apparent to one of ordinary skill in the art without undue experimentation and is chosen so that the resin becomes a cured/hardened non-swelling resin.

The silicone containing polymer does not require a curing agent. The silicone containing polymer should be chosen so that it hardens subsequent to its application to the QCM surface. This can be determined without undue experimentation.

In one embodiment, the curing agent is selected from the group consisting of: short chain aliphatic polyamines; oxyalkylated short chain polyamines; long chain polyamine adducts; aromatic polyamines; polyaminoamides; and polythiols.

Various types and combinations of organic materials are in a papermaking process. The methodologies embodied in the present disclosure serve to monitor the deposition of one or more organic materials/combinations of organic materials.

In one embodiment, the organic materials are hydrophobic.

In a papermaking process, organic materials include natural and/or synthetic contaminants. Under the guise of synthetic contaminants, there are stickies and tackies. White pitch is a common term that correlates to stickies and tackies.

In one embodiment, the stickies are microstickies.

In another embodiment, the microstickies do not exceed approximately 0.10-0.15 mm in size.

In another embodiment, the stickies and tackies are components of printing ink.

In another embodiment, the stickies and tackies are selected from the group consisting of: adhesives; coating binders; styrene butadiene rubber; ethylene vinyl acetate; polyvinyl acetate; polyvinyl acrylate; polyvinyl butyral; polybutadiene; wax; alkyd resins; polyol acrylates; and sizing chemicals.

Under the guise of natural contaminants, there is natural wood pitch. Deposition of one or more organic materials may be monitored at various locations in the papermaking process.

In one embodiment, the monitoring occurs in a papermaking process at a location selected from the group consisting of: pulp processing; recycling; a refiner, a repulper; a bleaching chest; a deinking stage; a water loop; a headbox of a paper or tissue machine, and a combination thereof.

Papermaking processes encompassed by this invention include, but are not limited to, board production, and papermaking processes that involve recycled pulp and/or broke.

The aqueous medium in a papermaking process includes liquids and slurries. In one embodiment, the aqueous medium is a pulp slurry.

In order to reduce deposition of organic materials in a papermaking process, various types of inhibitors are added to the papermaking process. The inhibitors serve to reduce/eliminate deposition of unwanted organic materials in a papermaking process. For example, there are many anti-pitch or anti-stickies treatments that are currently employed to reduce deposition of the organic materials. Therefore by using the protocols of this invention, the efficacy of these inhibitors can be determined. More specifically, paper chemistry programs may be developed based upon information obtained from the monitoring procedures of this invention. Moreover, feedback protocols may be developed to provide not only monitoring but control of chemistry added to the papermaking process so that the process becomes more cost-efficient, more efficacious, and produces a better paper product.

EXAMPLES

The following techniques were in utilized in the experiments discussed below. The method for coating the crystals used in the SRM and RQCM experiments was based on spin coating the epoxy resin onto the crystal when removed from the sensor. The crystals were cleaned of any organic contaminants by washing with acetone followed by 0.5N HCl and deionized water ("DI") water. The clean crystals were dried under a flow of nitrogen and fitted to a spin coater. The two-part epoxy resin was homogenized in acetone or tetrahydrofuran (THF) at a concentration of 10% by wt. The epoxy solution was deposited onto the top side of the crystal, covering the entire surface. The crystal was spun at 2500 revolutions per minute (RPM) for 50 seconds, yielding a thin layer of epoxy, which was allowed to cure at room temperature for three days.

In cases where the crystal was fixed in the instrument, a different approach was used to apply the epoxy coating. The surface of the crystal was cleaned in the same manner as the crystals for the SRM and RQCM, but the homogenized, two part epoxy was further diluted in acetone or THF to a concentration of 5% by wt. Roughly 100 microliters of this solution was dropped onto the surface of the crystal from approximately six inches above the crystal's surface to promote spreading of the solution. After rapid evaporation of the acetone, the resulting thin layer of epoxy deposited onto the crystal's surface was allowed to cure at room temperature for three days.

Protocol A

To simulate deposition, model stickies suspension consisting of emulsified acrylate microspheres was added to a suspension of pulp at 0.3 to 3% consistency. The effect of pulp consistency in the tested system on the rate of deposition is an important question related to the development of monitoring techniques for mill applications. The standard SRM batch system, which employs a magnetic stirrer, works well when the pulp is present at very low consistency, but it is not suitable to analyze higher-consistency slurries. This system was modified by using a wide propeller stirrer connected to a motor. The cell was firmly attached to a stand, and the stirrer was reaching the cell through a slot in the lid normally used by the heating rod. This system provided uniform stirring at 400 RPM of the pulp of up to 5% consistency.

An emulsion of microstickies consisting of an acrylic adhesive was pre-mixed into the stirring pulp slurry at a concentration of 0.25% by wt. of slurry. The mass deposition onto the crystal surface was then monitored with the SRM as a function of time. The effect of spiking a system with this adhesive emulsion during an ongoing experiment was also recorded. To observe the effects of deposit control chemistries, slurries dosed with the acrylic adhesive were also pre-treated with a stickies inhibitor and monitored in the same manner as the untreated experiments.

Protocol B

A specially designed flow cell was used in these experiments. This cell allows measurements to be made on flowing pulp slurries, as to mimic the conditions the sensor undergoes when installed at a paper mill. It is composed of a reserve of pulp slurry in a kettle fitted with a wide propeller stirrer connected to a motor and a drain valve. The valve is connected to a centrifugal pump that drives the flow of stock up through a 55 cm long tubular cell with an inner diameter of 2.6 cm, which has fittings to accommodate three individual QCM sensors and a temperature sensor. Upon exiting the flow cell, the slurry is guided back through a hose to the reserve kettle for recirculation. The deposition and temperature were recorded continuously on all three crystals using the Maxtek RQCM instrument. With this system, data was gathered on pulp slurries with consistencies comparable to the headbox consistency (0.1-0.5%). With three sensors exposed to the same flowing pulp suspension, the effectiveness of different coatings at attracting microstickies could be directly evaluated. To compare the epoxy coating described herein to an uncoated crystal and the polystyrene coating proposed by Tsuji et al. et al., *Method For Measuring Microstickies Using Quartz Crystal Microbalance With Dissipation Monitoring*, Kami Parupu Kenkyu Happyokai Koen Yoshishu 73, 126-129 (2006), the flow cell was fitted with these three sensors and stickies deposition from the flowing pulp slurry was monitored over time. This experiment demonstrated a significant advantage of the proposed method over that described in the literature. In a separate comparative study, the same three crystals were used to monitor deposition from whitewater in place of the flowing pulp slurry.

Protocol C

In this application, the RQCM is fitted to the cell described in Protocol B and is installed in the pulp line or paper/tissue machine (a sidestream connection), to assure a continuous flow of the slurry (mill water). The deposition is recorded continuously as the pulp slurry flows by the faces of the sensors at a rate of 2.0-3.0 gallons per minute (gpm).

Example 1

Figure 1:
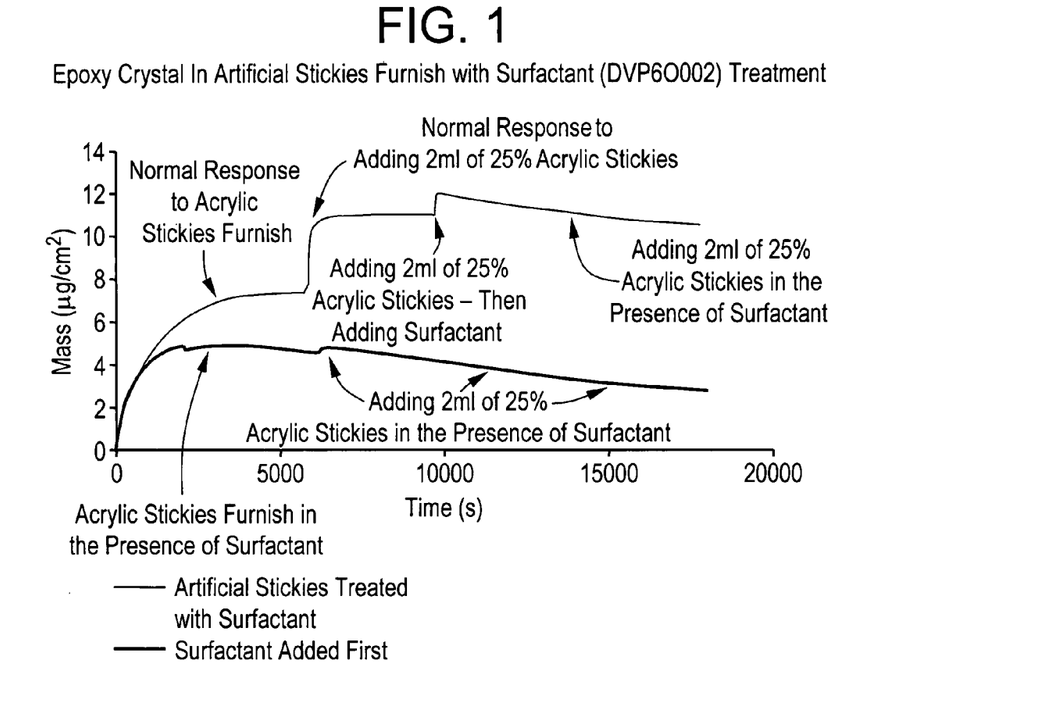
FIG. 1 is a graph that is related to Example 1.
Figure 2:
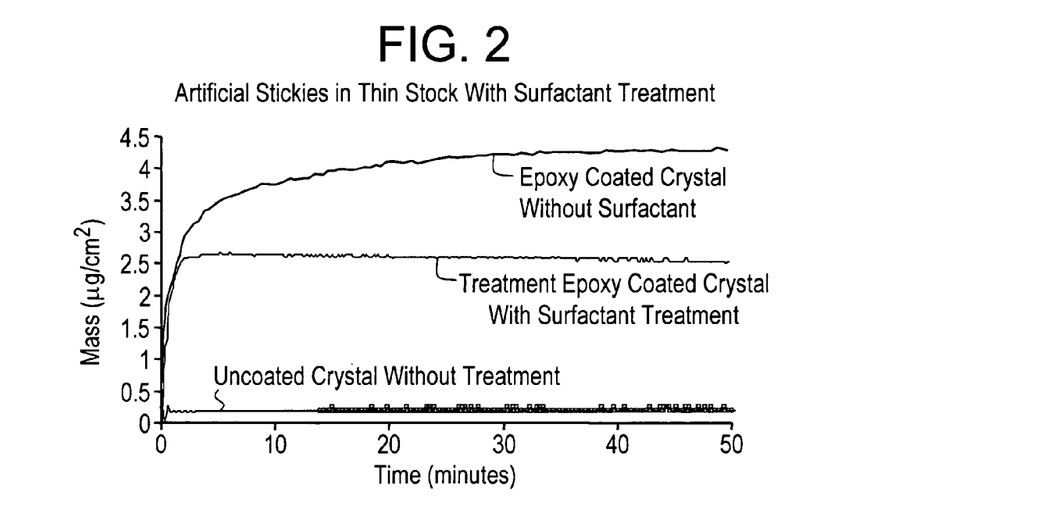
FIG. 2 is a graph that is related to Example 1.

Using the SRM per Protocol A, epoxy-coated crystals were screened for affinity to artificial stickies (acrylic adhesive) in the presence and absence of Nalco chemistries. With no treatment, the artificial stickies accumulated on the epoxy-coated crystal. As shown in FIG. 1 and FIG. 2, in presence of DVP6O002, a surfactant available from Nalco Company, Naperville, Ill., the artificial stickies have no affinity to the epoxy coated crystal.

Figure 3:
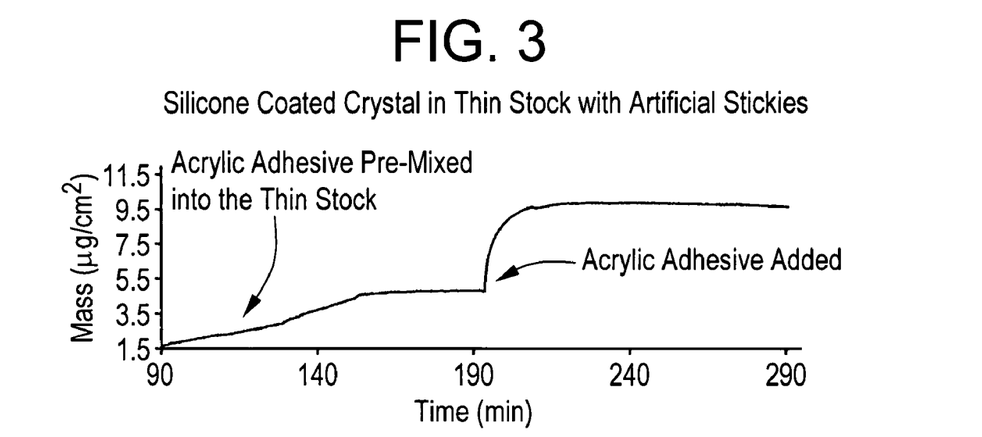
FIG. 3 is a graph that is related to Example 1.
Figure 4:
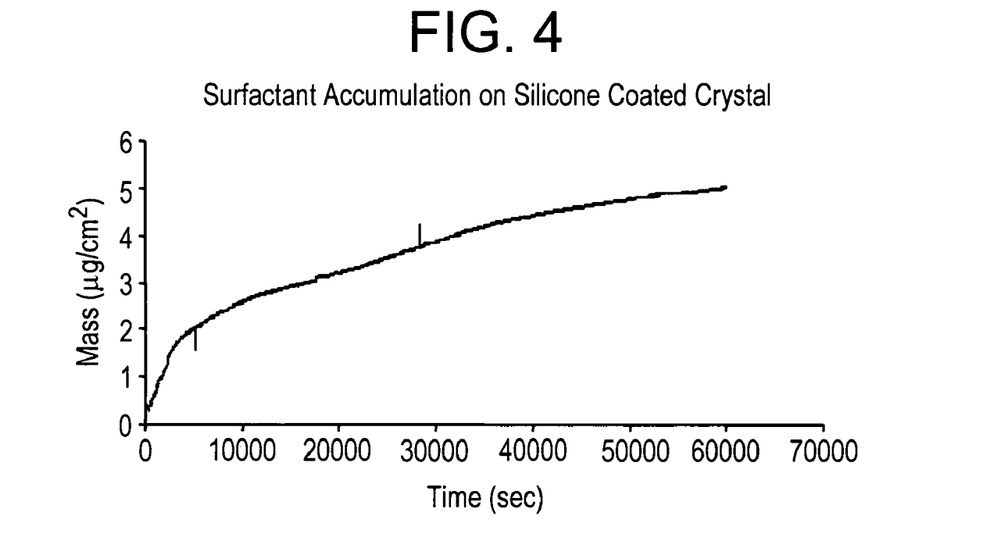
FIG. 4 is a graph that is related to Example 1.

As shown in FIG. 3, a possible alternative to the epoxy, a crystal was coated with room temperature vulcanizing (RTV) silicone, available from Dow Corning Corporation, tested positive for affinity to artificial stickies. In a blank experiment on a dilute pulp slurry containing surfactant DVP6O002, the mass was increasing over time, as shown in FIG. 4. Without surfactant, no mass increase is observed, so the hydrophobic RTV silicone coated crystal appears to be pulling the surfactant out of the slurry.

Figure 5:
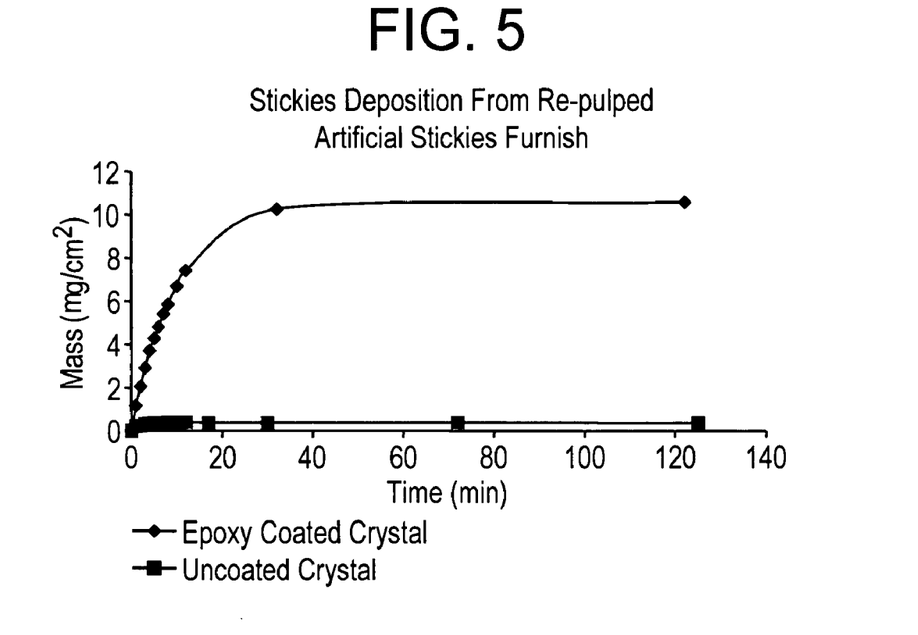
FIG. 5 is a graph that is related to Example 1.

In an attempt to test the crystal coatings for affinity to stickies of different compositions, an artificial stickies furnish was created by re-pulping Post-It® Notes, 3M Corporation, and adhesive labels with plain copy paper. The repulped furnish was diluted to a 0.5% consistency and tested with the epoxy coated and uncoated crystals using the RQCM. As shown in FIG. 5, the epoxy-coated crystal gathered a significantly higher amount of mass (stickies). The measurements were taken immediately after the samples came out of the repulper, and the majority of the mass on the crystal was accumulating in the first 30 minutes. To test if this was due to instability of the stickies after high shear forces from re-pulping, the slurry was stirred for 1.5 hours after re-pulping before measuring with the epoxy-coated crystal. A similar trend in deposition was observed, demonstrating the epoxy-coated crystal's ability to detect stickies that are stable in solution.

Example 2

Figure 6:
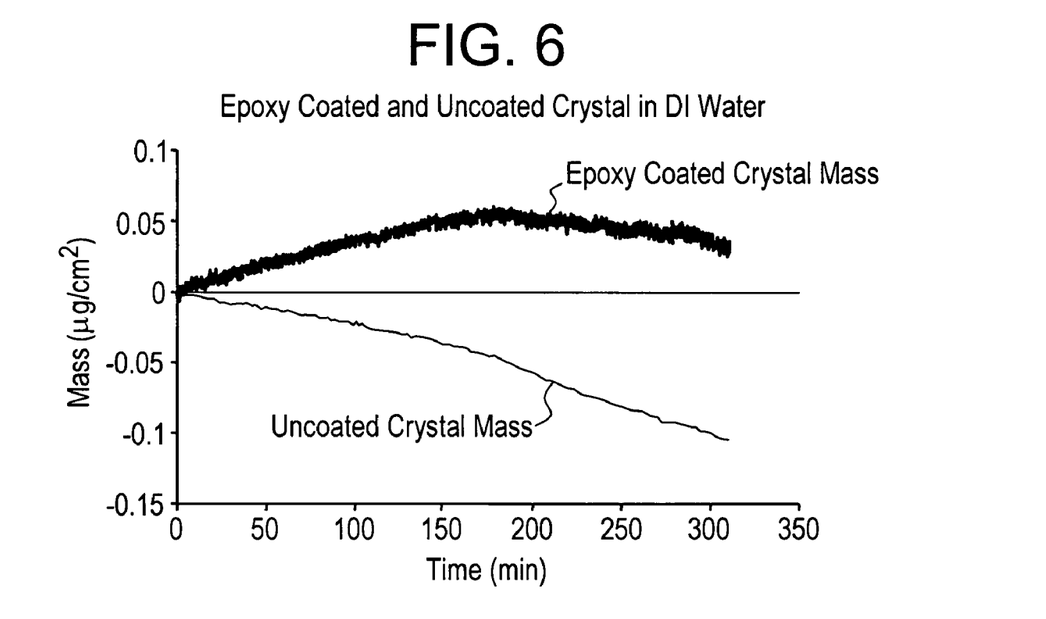
FIG. 6 is a graph that is related to Example 2.

Using Protocol B, the effects of swelling of the polymer coating in an aqueous environment were tested in deionized water and Kraft slurry (0.5% consistency) using the RQCM and the recirculation flow cell. As shown in FIG. 6, the results clearly show that the signal from swelling is minimal in comparison to the deposition observed from microstickies.

Example 3

Figure 7:
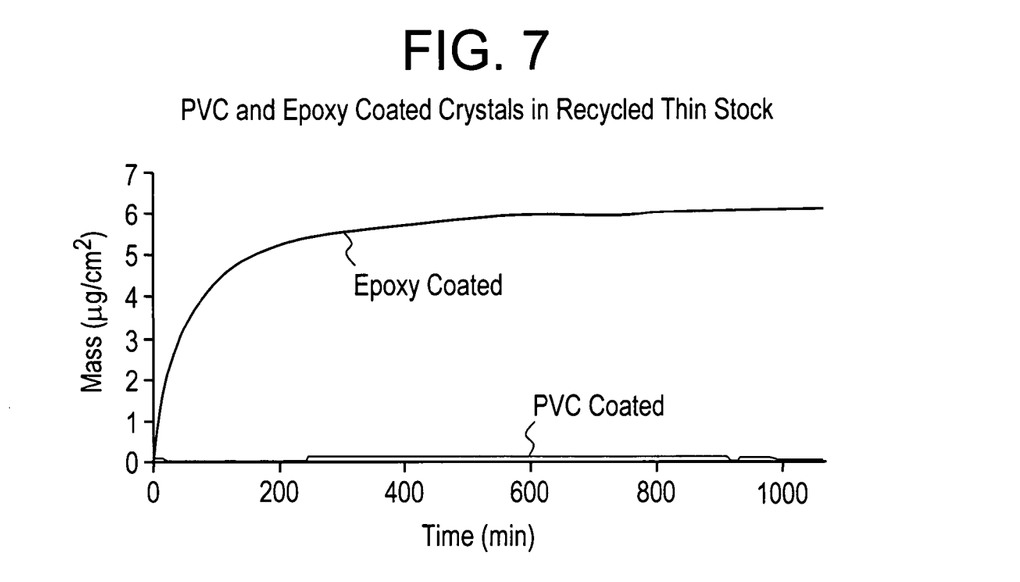
FIG. 7 is a graph that is related to Example 3.
Figure 8:
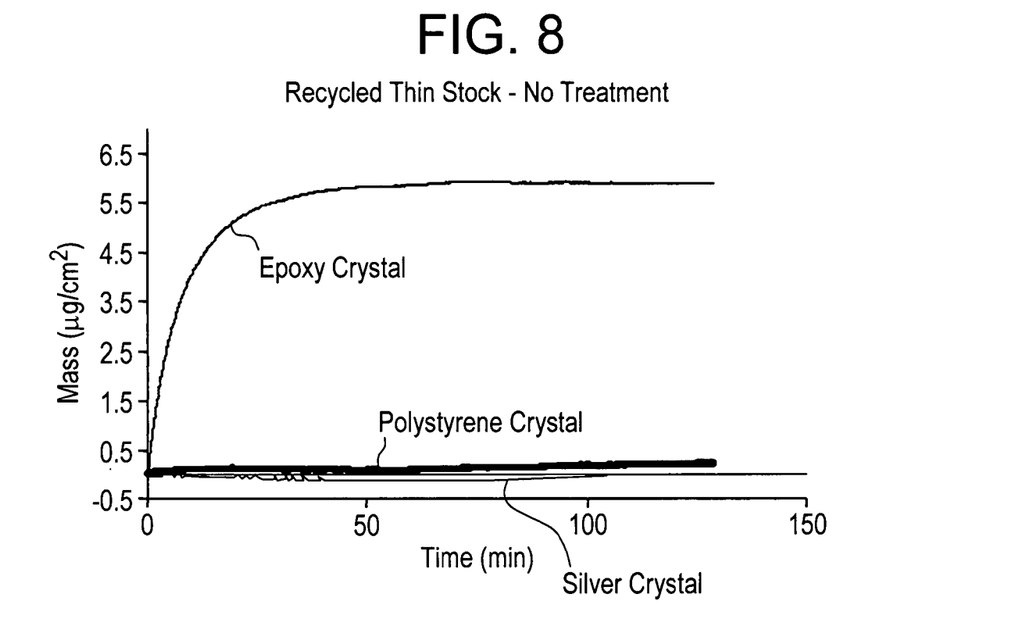
FIG. 8 is a graph that is related to Example 3.
Figure 9:
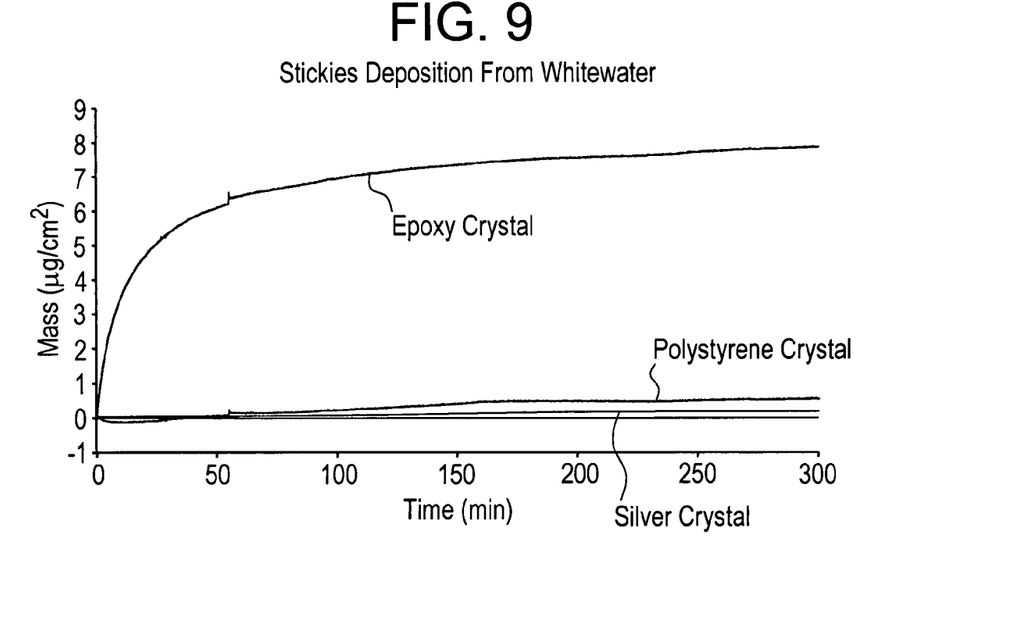
FIG. 9 is a graph that is related to Example 3.

Using Protocol B, coatings were screened for their effectiveness at attracting microstickies. The results are shown in FIGS. 7, 8, and 9. PVC and polystyrene shows no significant response as a coating to attract microstickies in either slurries or the less abrasive whitewater.

Figure 10:
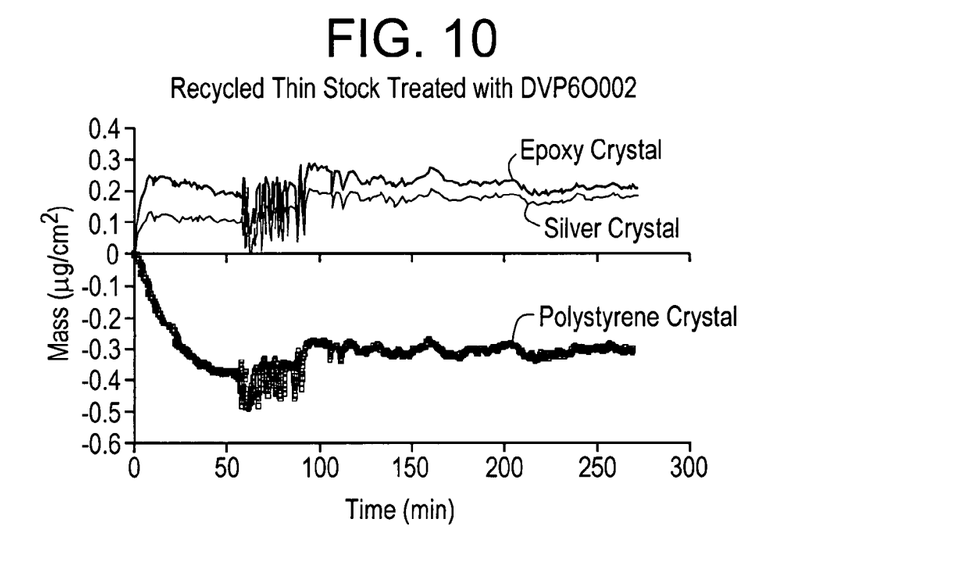
FIG. 10 is a graph that is related to Example 3.

As shown in FIG. 10, pre-treating the slurry with a surfactant before measuring reduces the deposition on the epoxy coated crystal by over 95%.

Example 4

Using the SRM per Protocol A, synthetic pitch accumulation was monitored in a benchtop experiment. A 1% synthetic pitch solution was prepared by mixing 5 g synthetic softwood pitch (a homogenized mixture of 50% abietic acid, 10% oleic acid, 10% palmitic acid, 10% corn oil, 5% oleyl alcohol, 5% methyl stearate, 5% beta-sitosterol, and 5% cholesteryl caproate) in 633 ml iso-propanol. 1 ml of this solution of was added to 10 L of DI water at pH 7.3. A solution of calcium chloride (5000 ppm as Ca ions, 50 ml) was added.

Figure 11:
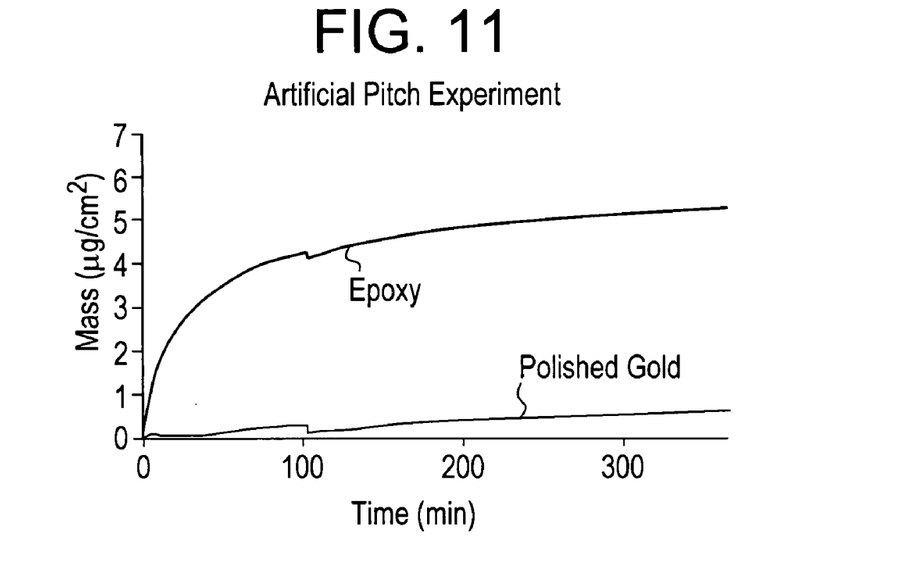
FIG. 11 is a graph that is related to Example 4.

As shown in FIG. 11, compared to the uncoated crystal with a polished gold surface, the epoxy coated crystal has an increased sensitivity for detecting wood pitch in an aqueous environment. Concentration of synthetic pitch was intentionally maintained at a very low level in this experiment. While wood pitch can be monitored using a QCM at high concentrations, it is not so at low concentrations. The experiment shows that the claimed method improves sensitivity of the method, thus making such monitoring possible.

Example 5

Figure 12:
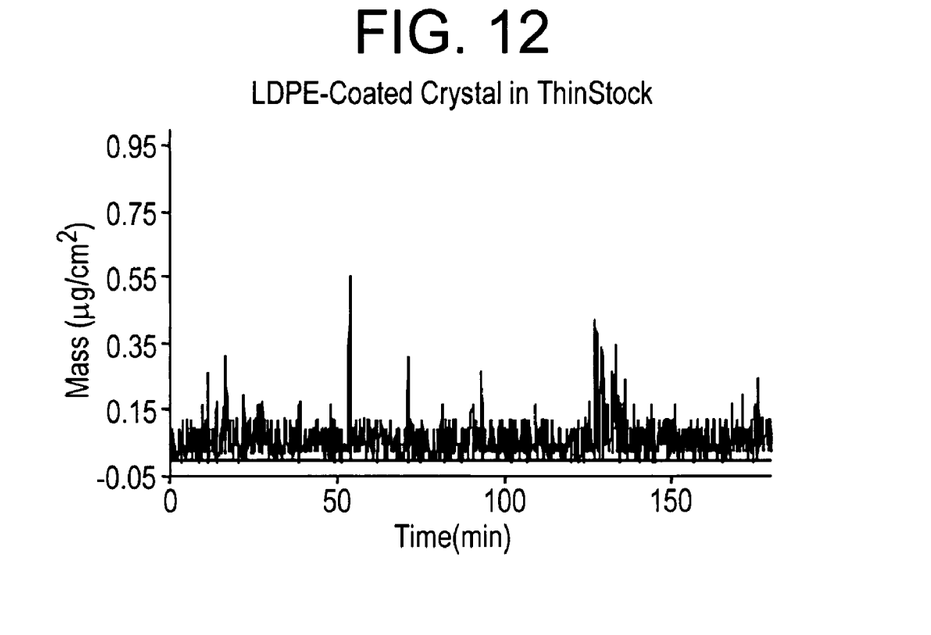
FIG. 12 is a graph that is related to Example 5.

Using the SRM per Protocol A, the low-density polyethylene (LDPE) was also tested as a crystal coating to attract microstickies from recycled furnish. The hypothesis was that the hydrophobic microstickies would be attracted to the highly hydrophobic LDPE coated crystal. The results in FIG. 12 show that this is not the case.

What is claimed is:

1. A method for monitoring the deposition of one or more organic materials dispersed in an aqueous medium in a papermaking process comprising: measuring the rate of deposition of the organic materials from the aqueous medium on-to a quartz crystal microbalance having a top side contacting with the aqueous medium coated with a layer containing a cured non-swelling epoxy resin or a silicone containing polymer, and a second, bottom side isolated from the aqueous medium.

2. The method of claim 1 wherein said papermaking process involves recycled pulp and/or broke.

3. The method of claim 1 wherein said organic materials are hydrophobic organic materials, stickies, tackies, white pitch, synthetic contaminants in a papermaking process, wood pitch, natural contaminants in a papermaking process, or a combination thereof.

4. The method of claim 3 wherein said stickies are microstickies.

5. The method of claim 4 wherein said microstickies do not exceed approximately 0.10-0.15 mm.

6. The method of claim 3 wherein said stickies and tackles are selected from the group consisting of: adhesives; coating binders; styrene butadiene rubber; ethylene vinyl acetate; polyvinyl acetate; polyvinyl acrylate; polyvinyl butyral; polybutadiene; wax; alkyd resins; polyol acrylates; and sizing chemicals.

7. The method of claim 1 wherein the top side of the quartz crystal microbalance is made of one or more conductive materials selected from the group consisting of: platinum; titanium; silver; gold; lead; cadmium;
diamond-like thin film electrodes with or without implanted ions; silicides of titanium, niobium and tantalum; lead-selenium alloys; mercury amalgams; and silicone.

8. The method of claim 1 wherein the resin is derived from epichlorohydrin and bisphenol A.

9. The method of claim 1 wherein said resin contains an aromatic backbone, aliphatic backbone, cycloaliphatic backbone, or a heterocyclic backbone.

10. The method of claim 1 wherein said resin is selected from the group consisting of: a cresol-novolac epoxy resin; a phenol novolac epoxy resin; a bisphenol F epoxy resin; a polynuclear phenol-glycidyl ether-derived resin; a tetraglycidylmethylenedianiline-derived resin; a triglycidyl-p-aminophenol derived resin; a triazine-derived resin; and a hydantoin epoxy resin.

11. The method of claim 1 wherein the silicone containing polymer is selected from the group consisting of: silicone rubber, and room temperature vulcanizing silicone rubber.

12. The method of claim 1 wherein the monitoring occurs in a papermaking process at a location selected from the group consisting of: pulp processing; recycling; a refiner, a repulper; a bleaching chest; a deinking stage; a water loop; a headbox of a paper or tissue machine, and a combination thereof.

13. The method of claim 1 wherein said aqueous medium is a pulp slurry.

14. A method for measuring the effectiveness of inhibitors that decrease the deposition of one or more organic materials in a papermaking process comprising:
   a. monitoring one or more organic materials dispersed in an aqueous medium in a papermaking process comprising measuring the rate of deposition of the organic materials from the aqueous medium onto a quartz crystal microbalance having a top side contacting the aqueous medium coated with a layer containing a non-swelling epoxy resin or a silicone containing polymer, and a second, bottom side isolated from the aqueous medium;
   b. adding an inhibitor that decreases the deposition of the organic materials from the aqueous medium; and
   c. re-measuring the rate of deposition of the organic materials from the aqueous medium onto the coated surface of the quartz crystal microbalance.

15. A method for measuring the effectiveness of inhibitors that decrease the deposition of one or more organic materials in a papermaking process comprising:
   a. monitoring one or more organic materials dispersed in an aqueous medium that simulates a papermaking process comprising measuring the rate of deposition of the organic materials from the aqueous medium onto a quartz crystal microbalance having a top side contacting the aqueous medium coated with a layer containing a non-swelling epoxy resin or a silicone containing polymer, and a second, bottom side isolated from the aqueous medium.
   b. adding an inhibitor that decreases the deposition of the organic materials from the aqueous medium; and
   c. re-measuring the rate of deposition of the organic materials from the aqueous medium onto the coated surface of the quartz crystal microbalance.

* * * * *